(12) United States Patent
Westlund et al.

(10) Patent No.: US 7,819,883 B2
(45) Date of Patent: Oct. 26, 2010

(54) METHOD AND APPARATUS FOR ENDOSCOPIC ACCESS TO THE VAGUS NERVE

(75) Inventors: Randy W. Westlund, River Falls, WI (US); David J. Smith, Shoreview, MN (US); Mark J. Bly, Falcon Heights, MN (US); Anthony V. Caparso, St. Louis Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 881 days.

(21) Appl. No.: 11/685,476

(22) Filed: Mar. 13, 2007

(65) Prior Publication Data

US 2008/0228194 A1 Sep. 18, 2008

(51) Int. Cl.
*A61N 1/02* (2006.01)
(52) U.S. Cl. ............................. 606/129; 607/118
(58) Field of Classification Search ............... 600/104, 600/183, 129, 101; 606/185, 190, 189; 607/115
See application file for complete search history.

(56) References Cited

U.S. PATENT DOCUMENTS

| | | | | |
|---|---|---|---|---|
| 3,941,121 | A * | 3/1976 | Olinger et al. | 600/167 |
| 4,602,624 | A | 7/1986 | Naples et al. | |
| 4,945,895 | A * | 8/1990 | Takai et al. | 600/104 |
| 5,352,222 | A | 10/1994 | Rydell | |
| 5,505,201 | A * | 4/1996 | Grill et al. | 600/371 |
| 5,895,353 | A | 4/1999 | Lunsford et al. | |
| 5,913,876 | A | 6/1999 | Taylor et al. | |
| 5,993,384 | A | 11/1999 | Lunsford et al. | |
| 6,004,262 | A * | 12/1999 | Putz et al. | 600/114 |
| 6,308,104 | B1 | 10/2001 | Taylor et al. | |
| 6,308,105 | B1 | 10/2001 | Duysens et al. | |
| 7,006,875 | B1 * | 2/2006 | Kuzma et al. | 607/118 |
| 2003/0040785 | A1 | 2/2003 | Maschino et al. | |

(Continued)

FOREIGN PATENT DOCUMENTS

WO 2006098996 9/2006

(Continued)

OTHER PUBLICATIONS

Web Site, Guidant, "VASOVIEW® 7×B™ and VASOVIEW® 7×S™ Endoscopic Vessel Harvesting System," http://www.guidant.com/products/ProductTemplates/CS/vasoview7.shtml, printed Mar. 13, 2007, pp. 1-2, VASOVIEW® 7×B™ pp. 1-20, VASOVIEW® 7×S™ pp. 1-20.

(Continued)

*Primary Examiner*—Carl H. Layno
*Assistant Examiner*—Jon-Eric C. Morales
(74) *Attorney, Agent, or Firm*—Faegre & Benson LLP (57) ABSTRACT

An apparatus for performing a minimally-invasive surgical procedure in the vagus nerve region includes a cannula, an endoscopic dissection tool and a cradle assembly slideably disposed in a cannula lumen. The cradle assembly includes a C-ring, an electrode cuff disposed over an exterior surface of the C-ring, and a deployment device. The electrode cuff is adapted to wrap around the target nerve region or nerve branch to be stimulated when deployed from the C-ring using the deployment device. A method of performing a minimally invasive surgical procedure is also described.

18 Claims, 8 Drawing Sheets

U.S. PATENT DOCUMENTS

| | | |
|---|---|---|
| 2003/0236558 A1 | 12/2003 | Whitehurst et al. |
| 2006/0030919 A1* | 2/2006 | Mrva et al. .................. 607/118 |
| 2006/0041283 A1* | 2/2006 | Gelfand et al. ................ 607/44 |
| 2006/0052856 A1* | 3/2006 | Kim et al. ................... 607/117 |
| 2006/0167498 A1 | 7/2006 | DiLorenzo |
| 2008/0172116 A1* | 7/2008 | Mrva et al. .................. 607/115 |

FOREIGN PATENT DOCUMENTS

WO    WO 2006098996 A1 *   9/2006

OTHER PUBLICATIONS

International Search Report and Written Opinion of international application No. PCT/US2008/051674, mailed Jun. 18, 2008, 14 pp.

* cited by examiner

METHOD AND APPARATUS FOR ENDOSCOPIC ACCESS TO THE VAGUS NERVE

TECHNICAL FIELD

This application relates generally to medical devices. More particularly, the present invention relates to an apparatus and a method for endoscopically accessing a nerve (e.g., the vagus nerve) to provide stimulation.

BACKGROUND

Minimally invasive surgical techniques, also sometimes referred to as endoscopic or laproscopic surgery, allow a surgical procedure to be performed on a patient's body through a relatively small incision in the body and with a limited amount of body tissue disruption. For patients, minimally invasive surgery means less trauma to the body, less blood loss, smaller surgical scars, and less need for pain medication. Patients leave the hospital sooner after minimally invasive surgery and return to normal activities sooner than with conventional surgery.

Despite their many advantages, such endoscopic procedures are often limited to procedures within accessible body lumens or cavities, which may be filled with clear liquid or insufflation with a gas to provide an open area within which to place the operative endoscope(s) and instrument(s).

Thus, there remains a need in the art for the development of new methods and apparatus for accessing other locations within the body, such as a vessel adjacent a nerve, to permit the performance of surgical and/or interventional procedures without the need for forming any open surgical incisions in the body.

SUMMARY

According to one embodiment of the present invention, a surgical apparatus for gaining access to a nerve region or nerve branch in a minimally invasive manner includes: a cannula including an elongated body having a proximal end and a distal end and at least one lumen extending a length of the body; a dissection tool including a viewing device and a tissue separating member; and a cradle assembly adapted to slide within the cannula lumen. The cradle assembly includes: a first leg and a second leg extending proximally from a C-ring generally adapted to cradle a portion of the nerve region or nerve branch; an electrode cuff adapted to be disposed over an exterior surface of the C-ring; and a deployment device adapted to deploy the electrode cuff from the C-ring.

According to another embodiment of the present invention, a surgical apparatus for use with a cannula including an endoscopic dissection tool to deploy an electrode cuff about a target nerve site including a cradle having a first leg and a second leg extending proximally from a C-ring generally adapted to cradle a portion of a nerve; an electrode cuff adapted to be disposed over an exterior surface of the C-ring; and a deployment device adapted to deploy the electrode cuff from the C-ring.

According to yet another embodiment, the present invention is a method of performing a minimally invasive surgical procedure using a surgical apparatus including a cannula, an endoscopic dissection tool, and a cradle assembly including a C-Ring having an electrode cuff disposed over an exterior surface of the C-Ring, wherein the electrode cuff is adapted to wrap around a target nerve region or nerve branch when deployed. The method includes: accessing a targeted nerve region; identifying and isolating potential target nerve regions or nerve branches; acutely stimulating potential target nerve regions or nerve branches; electing the target nerve region or branch to receive chronic stimulation; deploying the electrode cuff to the target nerve region or nerve branch; and chronically stimulating the target nerve region or nerve branch.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Minimally-invasive access tools for accessing a targeted site within a patient's anatomy in a minimally invasive manner are well known. Typical minimally-invasive access tools include a cannula which is inserted into a small incision in the patient's body. The cannula holds the incision open and serves as a conduit extending between the exterior of the body and the local area inside the body where a procedure is to be performed. The cannula includes a tubular body having a proximal end and a distal end. At least one lumen extends the length of the body into which a number of surgical tools including viewing devices can be inserted as necessary or desired to complete the procedure. Exemplary minimally-invasive surgical access tools are shown and described in U.S. Pat. No. 5,895,353 and U.S. Pat. No. 6,176,825, both of which are herein incorporated by reference.

Figure 1:
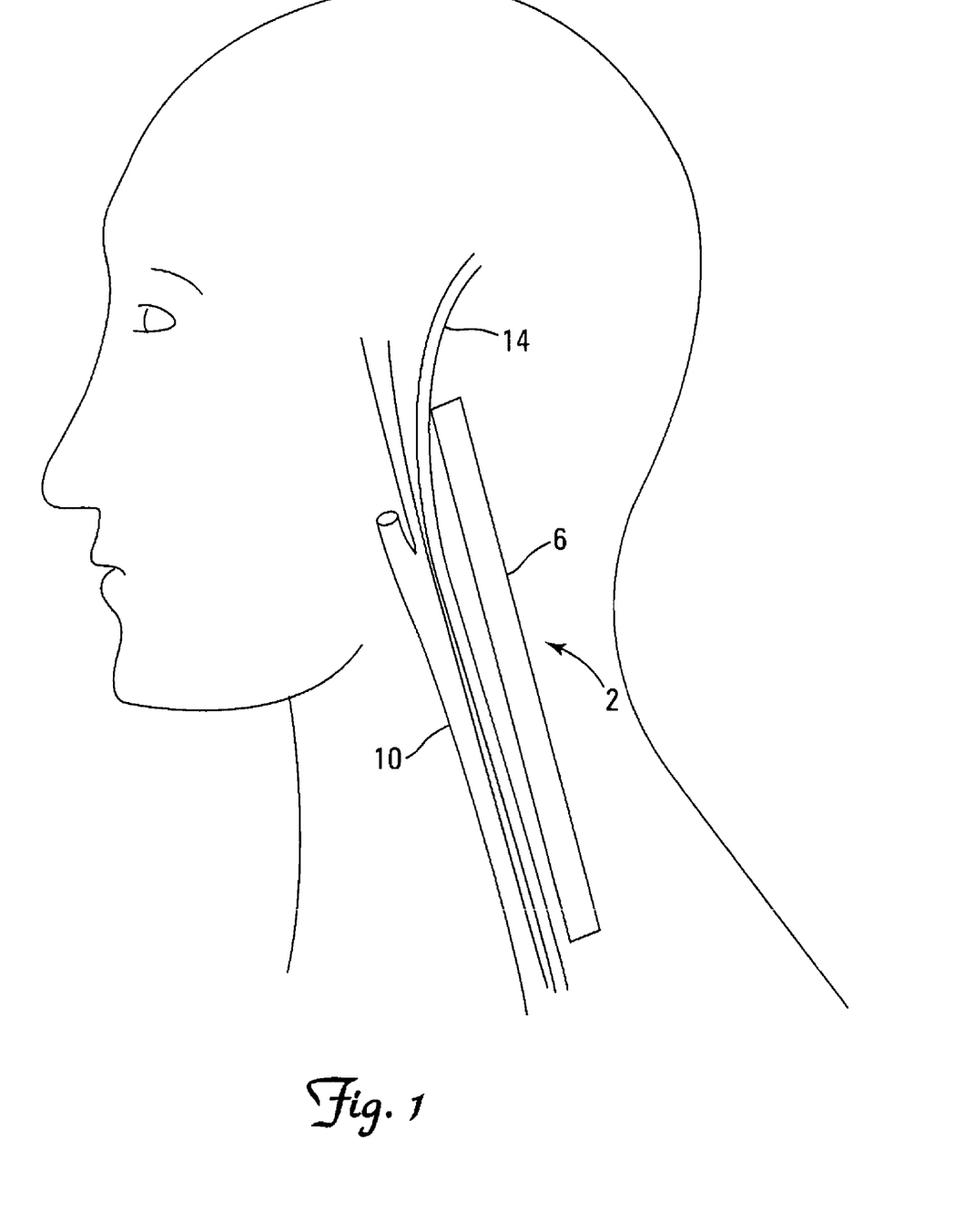
FIG. 1 is a partial schematic view of a patient's anatomy including the internal jugular vein, vagus nerve, and common carotid artery.

FIG. 1 is a partial schematic view of a region of a patient's anatomy where minimally invasive access is desired. FIG. 1 is a schematic view of a patient's carotid sheath 2. The three major structures included in the carotid sheath 2 are the internal jugular vein 6, the common carotid artery 10, and the vagus nerve 14. As shown in FIG. 1, the vagus nerve 14 lies adjacent the common carotid artery 10. According to one embodiment, access to the carotid sheath 2 is gained through a small incision made in a patient's neck region. A cannula is introduced in the small incision and the region is insufflated to assist in viewing the vagus nerve 14 and its various branches.

Figure 2A:
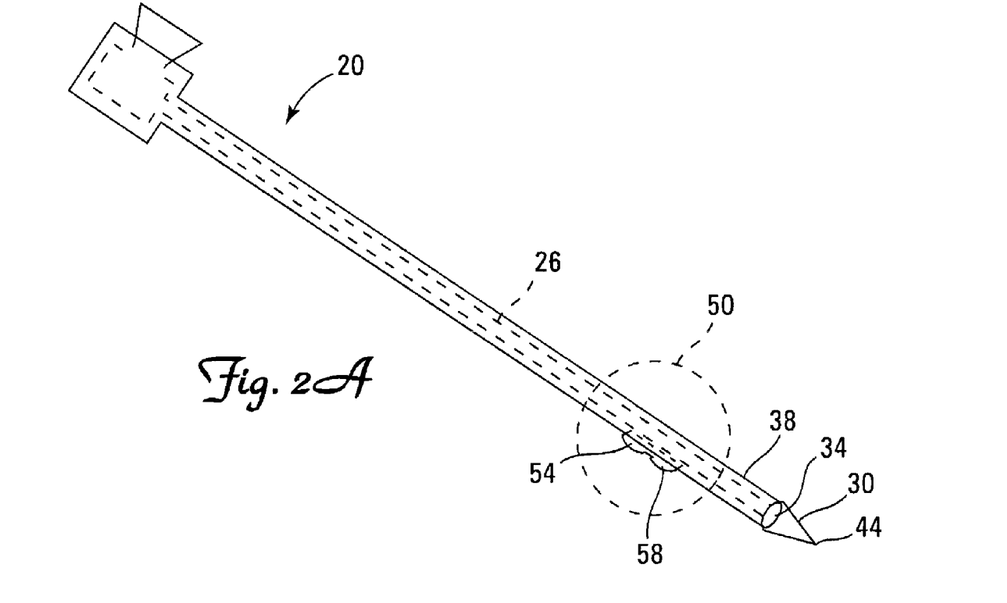
FIG. 2A is a side schematic view of a dissection tool including a viewing device according to an embodiment of the present invention.

FIG. 2A is a schematic view of an endoscopic dissection tool 20 adapted to be inserted through the cannula lumen. Dissection tools such as the one represented in FIG. 2A are well known in the art. Typically, the dissection tool 20 includes a viewing device 26 (represented by the dashed lines in FIG. 2A) and a tissue separating member 30. The viewing device 26, according to one exemplary embodiment, includes optical fibers or a charged coupled device camera. Other viewing devices known to those of skill in the art may also be used. Additionally, the viewing device 26 may include a lighted, viewing end 34 located near a distal end 38 of the dissection tool 20. The tissue separating member 30 can be transparent and has a blunt, conical tip 44 adapted to separate tissue as the dissection tool 20 is advanced on a path adjacent the nerve 14. Alternatively, the dissection tool 20 can be advanced along a path that is substantially perpendicular to the nerve to be accessed. One of skill in the art would recognize that minor modifications to the dissection tool 20 and its various members described below may be needed in order to accommodate a perpendicular approach. The tissue separating member 30 is used to breach the carotid sheath 2 thus gaining access to the vagus nerve 14. Alternatively, a small incision may be made in the patient's neck region and the carotid sheath 2 surgically opened. Using visualization techniques along with insufflation of the region, the various branches of the vagus nerve 14 are viewed and identified. Additionally, the dissection tool 20 can be used to further isolate the surrounding tissue from the nerve 14 and the nerve branches.

Figure 2B:
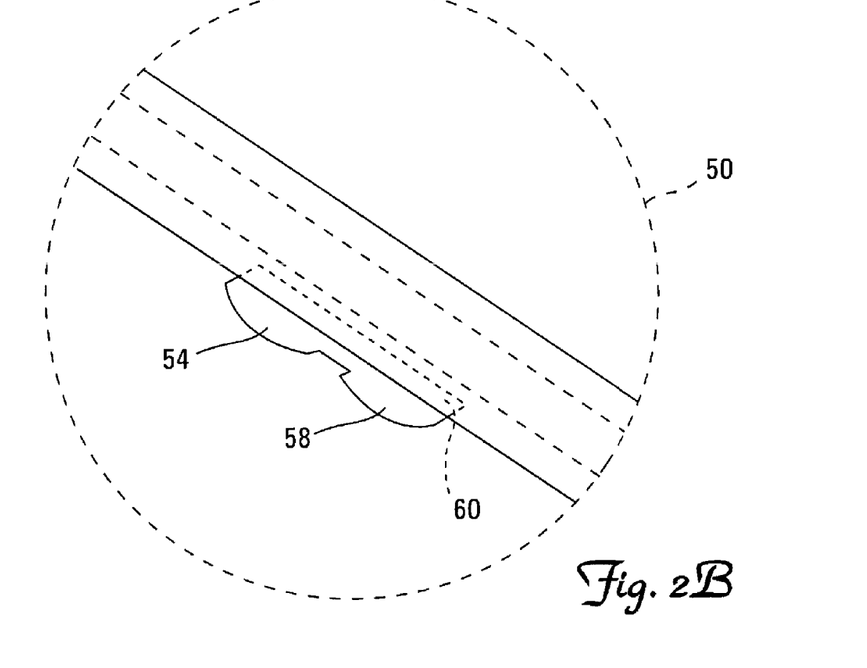
FIG. 2B is a close-up schematic view of a distal end of the dissection tool shown in FIG. 2A according to a further embodiment of the present invention.

FIG. 2B is a close-up schematic view of a distal region 50 of the endoscopic dissection tool 20 shown in FIG. 2A. According to the embodiment of the present invention, shown in FIG. 2B, the dissection tool 20 includes at least one electrode adapted to acutely stimulate a nerve. According to one exemplary embodiment, the dissection tool 20 includes two electrodes one of which can be an anode 54 and one of which can be a cathode 58. The electrodes can be electrically coupled to an external stimulator. The electrodes are used to acutely stimulate a nerve region or nerve branch as the dissection tool 20 is advanced along the nerve 14. This acute stimulation is used to determine an optimal stimulation threshold as well as to identify and select the optimal target nerve region or nerve branch to achieve a desired result or effect. Once the target nerve region or branch has been identified through acute stimulation, other electrodes adapted to chronically stimulate a nerve can be deployed to the target nerve region, as will be described in further detail below. According to one embodiment of the present invention, the anode 54 and cathode 58 are located on an exterior surface of the endoscopic dissection tool 20. Alternatively, the dissection tool 20 includes an aperture 60 located in proximity to the distal end 38 of the tool 20. The anode 54 and the cathode 58 can be extended through the aperture 60 such that they are placed in closer proximity to the nerve region or nerve branch to be stimulated.

One or more surgical tools for further isolating and manipulating a nerve region or nerve branch can be inserted through the cannula lumen or lumens as desired at any time during the procedure. These tools can include, but are not limited to, the following: shavers, dissectors, scissors, forceps, bipolar cautery forceps, retractors, dilators, and evacuators.

Figure 3A:
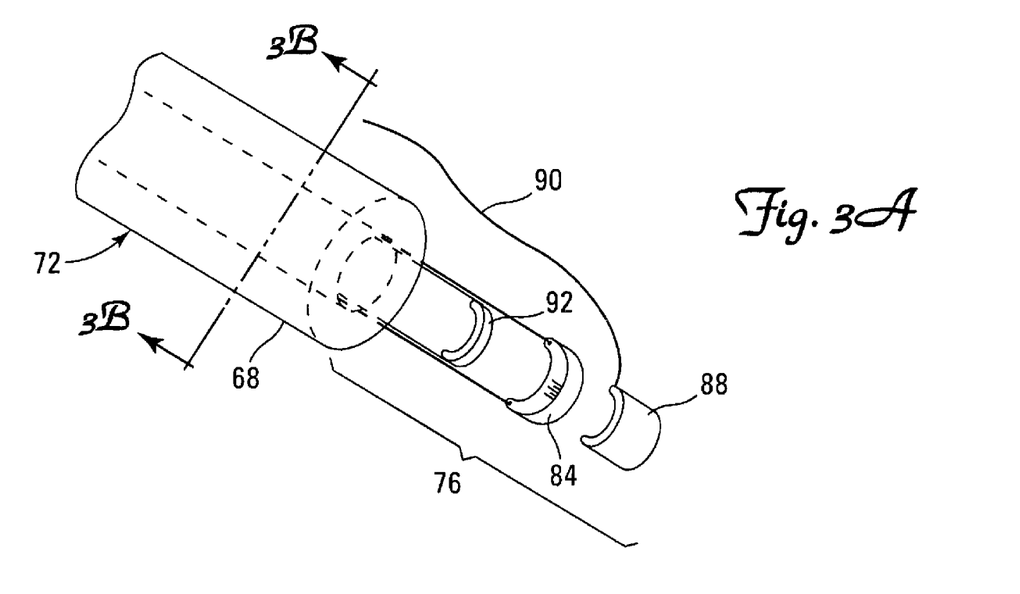
FIG. 3A is a schematic view of a distal end of a surgical apparatus including a cradle assembly according to an embodiment of the present invention.
Figure 3B:
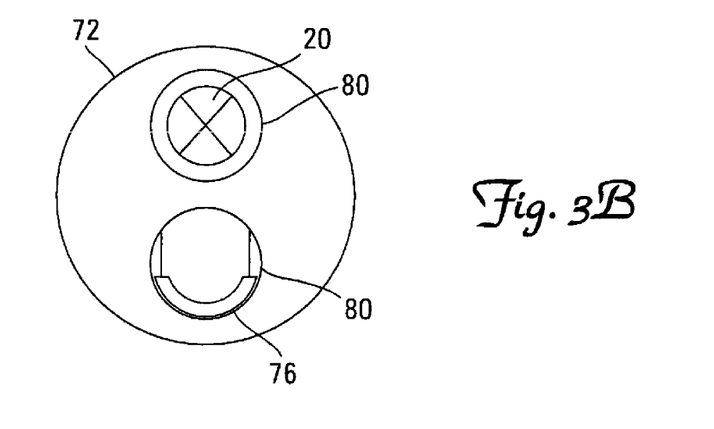
FIG. 3B is a cross-sectional view taken along line 3B-3B of the surgical apparatus shown in FIG. 3A.

FIG. 3A is a schematic view of a distal end 68 of the cannula 72 including a cradle assembly 76. FIG. 3B is a cross-sectional view of the distal end 68 of the cannula 72 shown in FIG. 3A including the cradle assembly 76 disposed in a cannula lumen 80. The cradle assembly 76 is adapted to slide and rotate within the lumen 80. According to one embodiment of the present invention, the cradle assembly 76 can be sized such that it is adapted to be inserted into the same lumen 80 as a viewing device such as the endoscopic dissection tool 20 described above. Alternatively, the cannula 72 includes an endoscopic lumen for housing a viewing device and one or more additional lumens 80 for accommodating a variety of surgical tools including the cradle assembly 76, as shown in FIG. 3B.

As shown in FIG. 3A, the cradle assembly 76 includes a cradle 84, an electrode cuff 88 electrically coupled to a lead 90, and a deployment device 92. The electrode cuff 88 is disposed over the cradle 84. The deployment device 92 is used to push or deploy the electrode cuff 88 from the cradle 84 and onto the target nerve region or nerve branch. The cradle assembly 76 may be configured to accommodate different approach angles or paths used to gain access to the target nerve region or nerve branch.

Figure 4A:
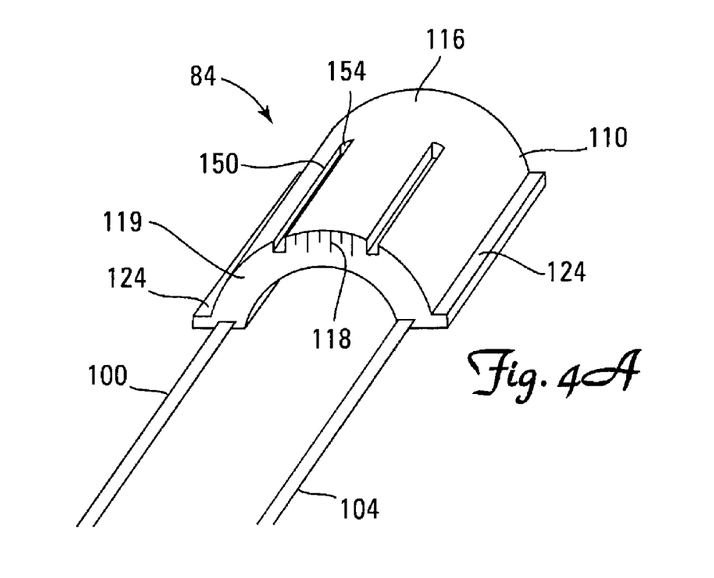
FIG. 4A is a perspective view of an exterior surface of a C-ring according to one embodiment of the present invention.
Figure 4B:
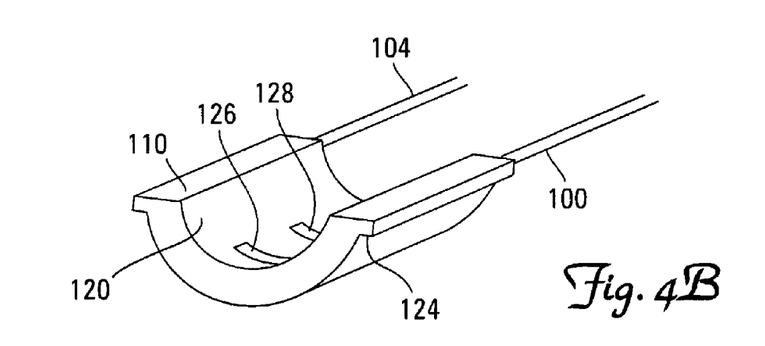
FIG. 4B is a perspective view of an interior surface of the C-ring shown in FIG. 4A according to one embodiment of the present invention.

FIGS. 4A and 4B are close-up schematic views of the cradle 84. According to one embodiment of the present invention, as shown in FIGS. 4A and 4B, the cradle 84 comprises a first leg 100 and a second leg 104 extending proximally from a C-ring 110 coupled thereto. The C-ring 110 includes an exterior surface 116 (shown in FIG. 4A) and an interior surface 120 (show in FIG. 4B). According to one embodiment of the present invention, the exterior surface 116 is slightly flattened. Alternatively, the exterior surface 116 is arcuate and can include one or more retaining ledges 124 adapted for assisting retention of the electrode cuff 88 on the exterior surface 116. According to a further embodiment of the present invention, the C-ring 110 also can include scaling marks 118 located on a proximal face 119 to assist in estimating the size of the nerve region or nerve branch onto which an electrode cuff will be deployed. The scaling marks 118 are situated on the C-ring 110 such that they are able to be viewed with the viewing device disposed either in a same or a different lumen 80.

According to a further embodiment of the present invention, the interior surface 120 of the C-ring 110 is also arcuate. The interior surface 120 of the C-ring 110 may, for example, be shaped such that the interior surface 120 of the C-ring 110 generally conforms to an exterior surface of a nerve region or a nerve branch. The arcuate shape of the interior surface 120 allows the C-ring 110 to be rotated about the nerve region or nerve branch assisting in further manipulation or isolation of the nerve. The arcuate shape of the interior surface 120 also assists in positioning the C-ring 110 around the nerve region or branch to be stimulated.

According to yet another embodiment of the present invention, as shown in FIG. 4B, the interior surface 120 of the C-ring 110 includes one or more electrodes adapted to acutely stimulate the nerve region or branch in order to identify and select a target nerve region or branch. For example, the interior surface 120 of the C-ring 110 includes at least one anode 126 and one cathode 128 for acutely stimulating a nerve region or branch. The anode 126 and the cathode 128 can be electrically coupled to an external stimulator via a conductor. According to one embodiment of the present invention, the conductors are disposed within at least one of the legs 100 or 104 to which the C-ring 110 is coupled. Stimulation is used to determine an optimal stimulation threshold as well as identify the target nerve region or branch to be stimulated such that a desired result is achieved. To acutely stimulate the nerve region or branch, the C-ring 110 is extended beyond the distal end 68 of the cannula 72 and advanced along a nerve region or branch under endoscopic visualization. The C-ring 110 including the electrodes 126 and 128 can be further rotated around the nerve region or nerve branch as necessary or desired until a desired nerve region or branch to be stimulated is identified using acute stimulation.

Figure 4C:
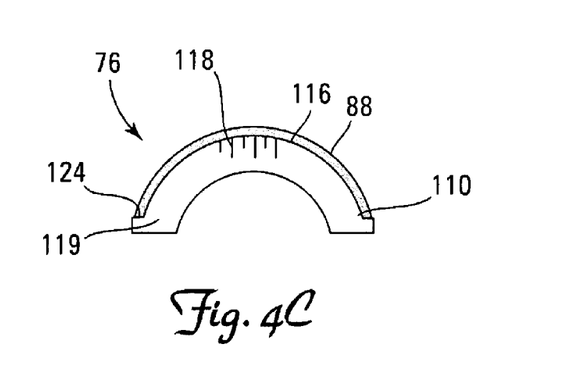
FIG. 4C is an end plan view of a proximal end of the C-ring shown in FIGS. 4A and 4B, according to an embodiment of the invention, including an electrode cuff.

As shown in FIGS. 3A and 4C, the cradle assembly 76 also includes an electrode cuff 88 disposed over the exterior surface 116 of the C-ring 110. According to one embodiment of the present invention, the electrode cuff 88 is a modified split cylinder electrode cuff. The electrode cuff 88 can be appropriately sized to wrap around or to conform to a variety of nerves or nerve braches. The electrode cuff 88 is made from a flexible material having a preformed, substantially cylindrical shape adapted to wrap, at least partially, around the target nerve region or branch upon deployment from the C-Ring 110 in order to chronically stimulate the nerve. The material should be sufficiently elastic such that the elastic forces of the material allow the electrode cuff 88 to be held in position about the nerve or nerve branch. According to yet a further embodiment of the present invention the electrode cuff 88 can be configured to wrap around a nerve complex or bundle. For example, the electrode cuff 88 can be configured such that it is of sufficient size and elasticity to wrap around large nerve complexes such as the femoral nerve complex.

Figure 5A:
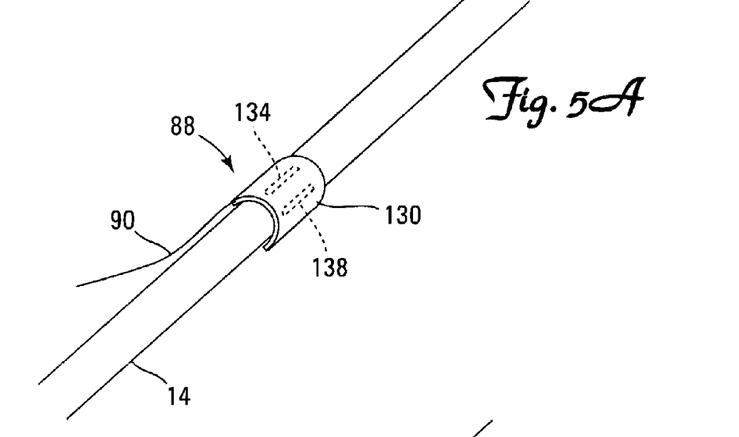
FIGS. 5A-5C are schematic views of an electrode cuff according to various embodiments of the present invention.
Figure 5B:
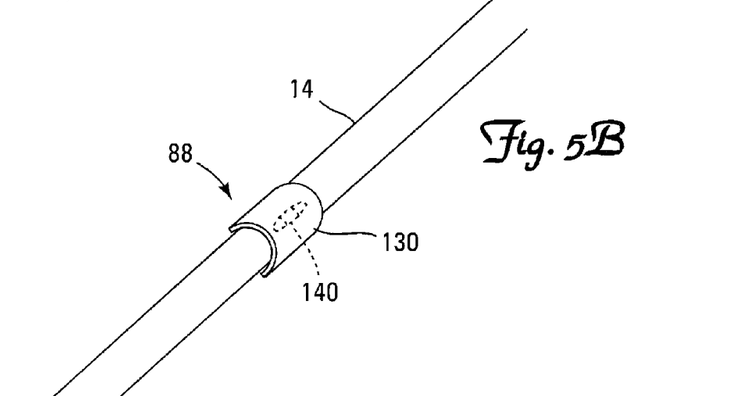
Figure 5C:
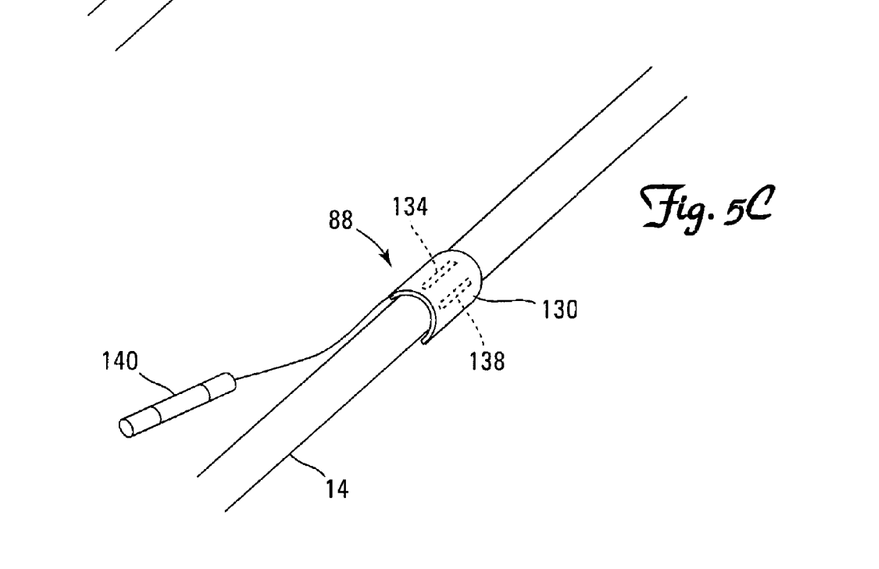

FIGS. 5A-5C are schematic views of an electrode cuff 88 according to various embodiments of the present invention. Typically, the electrode cuff 88 is electrically coupled to a lead 90. According to one embodiment of the present invention, the electrode cuff 88 includes a self-curling sheet 130 of flexible material having a pre-formed shape adapted to wrap around a nerve region or branch when deployed from the exterior surface 116 of the C-ring. Additionally, the electrode cuff 88 includes one or more electrodes disposed on an interior surface 132, such as an anode 134 and a cathode 138 (represented by dashed lines in FIG. 5A), adapted to chronically stimulate the selected nerve region or nerve branch identified through acute stimulation. According to an alternative embodiment of the present invention, as shown in FIG. 5B, the electrode cuff 88 includes a microstimulator 140 disposed on the interior surface 132 of the electrode cuff 88. Alternatively, as shown in FIG. 5C, the microstimulator 140, is tethered to an end of the cuff 88.

Figure 6A:
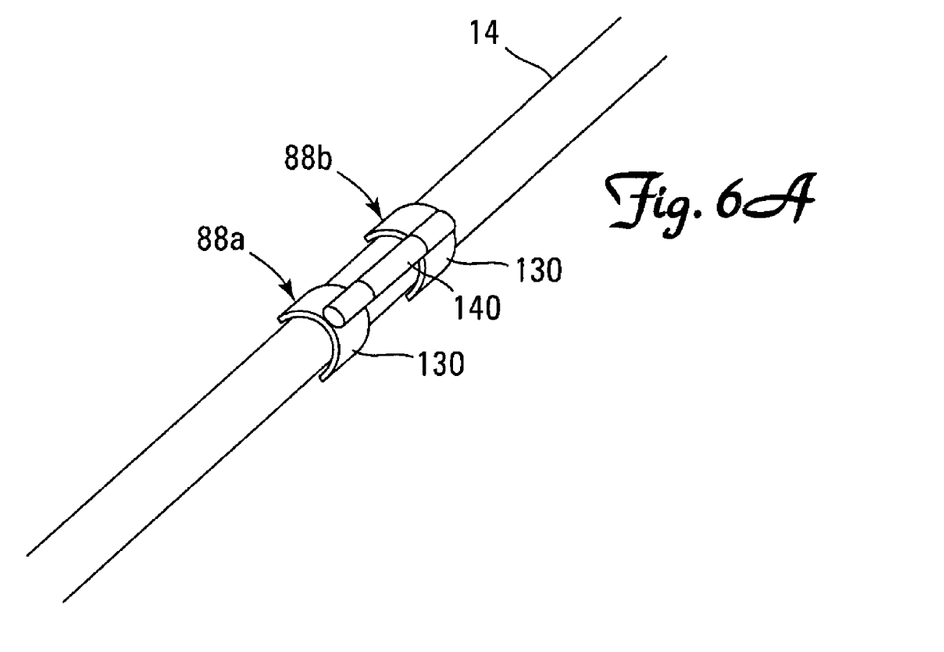
FIGS. 6A-6B are schematic views of at least one electrode cuff coupled to a microstimulator according to alternative embodiments of the present invention.
Figure 6B:
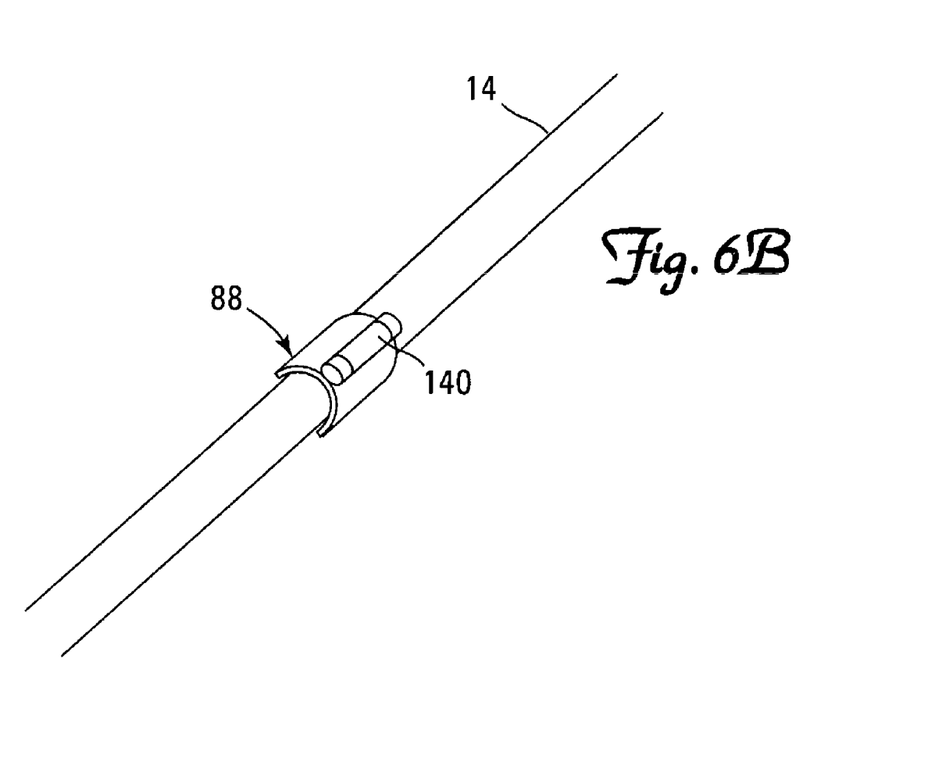

FIGS. 6A and 6B are schematic views of a microstimulator coupled to an exterior of at least one electrode cuff 88. According to one exemplary embodiment, as shown in FIG. 6A, the microstimulator 140 is coupled to an exterior surface of a single electrode cuff 88. At least one electrode is disposed on the interior surface of the electrode cuff 88 and is in electrical communication with the microstimulator 140.

According to an alternative exemplary embodiment of the present invention, a microstimulator 140 is coupled to two electrode cuffs 88a and 88b. The electrode cuffs 88a and 88b each include a self-curling sheet 130 of flexible material having a pre-formed shape adapted to wrap around a nerve region or branch when deployed from the exterior surface 116 of the C-ring. The C-ring can be appropriately sized and configured to accommodate dual electrode cuffs 88a and 88b. The dual electrode cuffs 88a and 88b coupled to the microstimulator 140 are deployed from the C-ring in a similar manner as described above. Each electrode cuff 88a and 88b includes a single electrode in electrical communication with the microstimulator 140. For example, electrode cuff 88a includes the cathode and electrode cuff 88b includes the anode.

With reference to the embodiments shown in FIGS. 5B-6B, the microstimulator 140 typically includes a power source, appropriate control circuitry, and a communication element disposed therein. According to a further embodiment of the present invention, the microstimulator 140 can include telemetry for wirelessly communicating with a pulse generator or some other external device. The microstimulator 140 is programmed to deliver appropriate therapy to the target nerve site through the electrode cuff 88. An exemplary microstimulator is shown and described in U.S. Pat. No. 5,324,316, which is herein incorporated by reference.

Figure 7A:
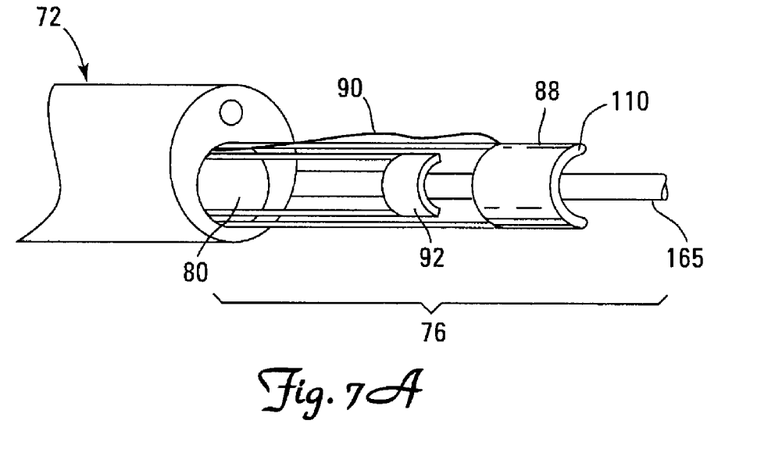
FIGS. 7A-7C are schematic views of a cradle assembly during deployment of an electrode cuff to a target nerve site according to an embodiment of the present invention.
Figure 7B:
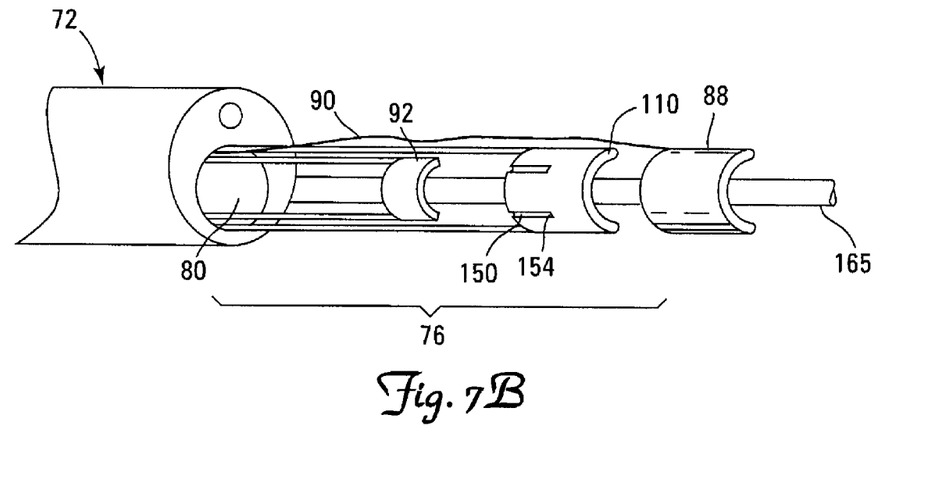
Figure 7C:
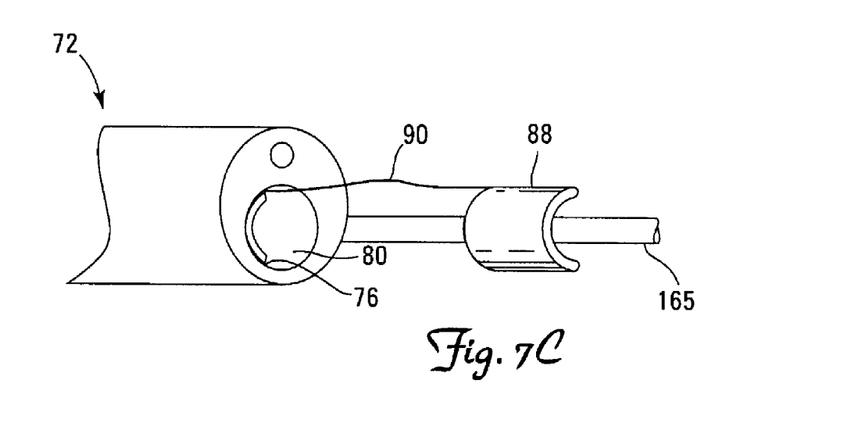

FIGS. 7A-7C are schematic views of the cradle assembly 76 during various stages of deployment of the electrode cuff 88 to a targeted nerve region or branch 165 after the surrounding tissue has been removed. The deployment device 92 is used to push the electrode cuff 88 from the exterior surface 116 of the C-ring 110 onto the targeted nerve region or branch 165 to receive chronic stimulation. The deployment device 92 has an interior surface 148 generally conforming to the exterior surface 116, shown in FIG. 4C, of the C-ring 110. Prior to deploying the electrode cuff 88 from the exterior surface 116 of the C-ring 110, according to one exemplary embodiment, the deployment device 92 is adapted to rest on the C-ring 110 at a position proximal to a trailing edge of the electrode cuff 88. According to another embodiment of the present invention, the deployment device 92 slides along a groove or track 150 formed in the exterior surface 116 of the C-ring 110 such that the movement of the deployment device 92 can be controlled. A stop 154 can be provided at the distal end of the track 150 to prevent over extension of the deployment device 92 and to further control its movement. Once the electrode cuff 88 has been deployed, the deployment device and the C-ring can be retracted and/or removed from the cannula lumen.

Figure 8:
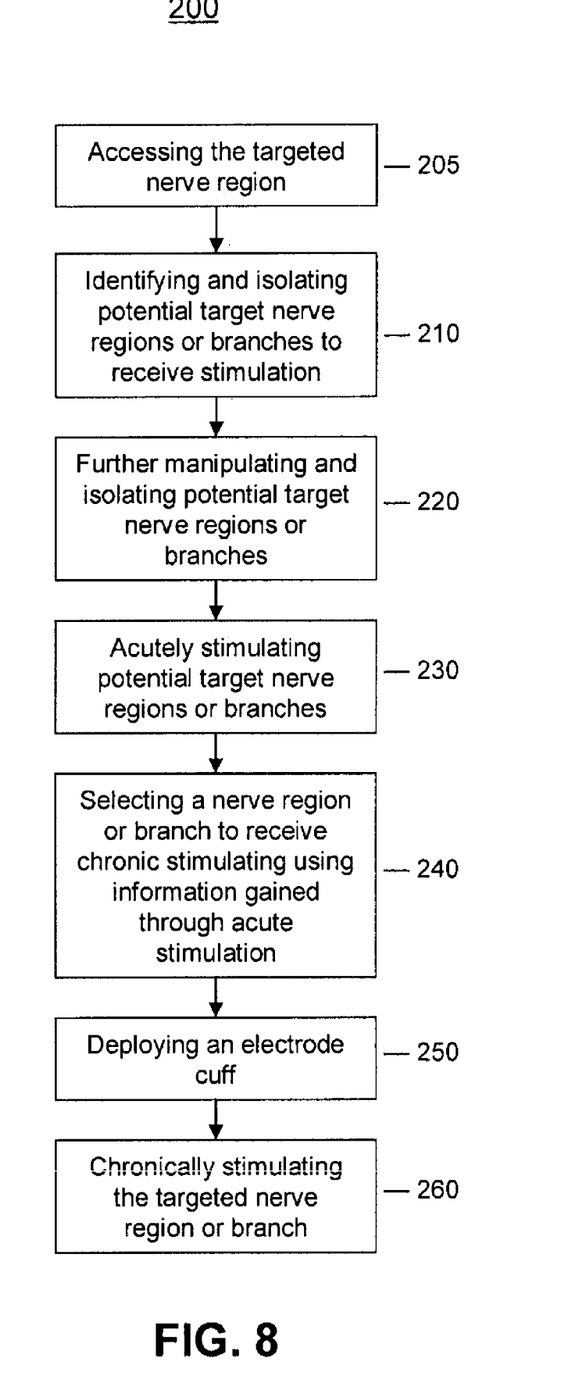
FIG. 8 is a block diagram of a method of using a surgical apparatus according to yet another embodiment of the present invention.

FIG. 8 is a block diagram showing a method 200 of performing a surgical procedure, according to an embodiment of the present invention, employing a surgical apparatus including a cannula and a cradle assembly. A single incision is made, for example, in the mid-cervical region of a patient's body. A cannula is inserted into the incision to form a conduit between the exterior of the patient's body and the local region where access is desired, for example, in the region of a patient's vagus nerve 14. Using an endoscope or other viewing device inserted through a cannula lumen, the vagus nerve 14 is identified in the carotid sheath 2. The dissection tool 20 is introduced into the incision through the cannula and is used to breech the carotid sheath 2 to gain access to the vagus nerve 14 (block 205). Once inside the carotid sheath 2, the dissection tool 20 is advanced along the vagus nerve 14, bluntly dissecting tissue away from the nerve 14 using the blunt, conical dissection tip 44. Various nerve regions and nerve branches are identified during the dissection process and can be further isolated for stimulation and/or electrode deployment (block 210). Once the desired nerve regions and/or branches have been isolated, additional nerve manipulation and dissection is performed as necessary or desired to prepare potential stimulation nerve regions or branches to receive the electrode cuff (block 220). The additional nerve manipulation and dissection can be performed using any number of a variety of surgical tools that can be interchangeably inserted through the cannula lumen. Potential target nerve regions or branches are acutely stimulated using electrodes located on either the dissection tool 20 or the interior surface of the C-Ring forming the cradle assembly 76 (block 230). Potential target nerve regions or branches are acutely stimulated to determine an optimal stimulation threshold and/or determine whether a desired result is achieved. Using the information achieved through acute stimulation, the acutely stimulated potential target nerve regions and/or branches are assessed for their value and/or appropriateness for receiving chronic therapy (block 240). Once a target nerve region or nerve branch is selected to received chronic stimulation therapy, the cradle assembly can be positioned such that the electrode cuff can be accurately deployed and chronic stimulation therapy to the targeted nerve region or branch can be delivered (blocks 250 and 260).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A surgical apparatus for gaining access to a nerve region or nerve branch in a minimally invasive manner, the apparatus comprising:
    a cannula including an elongated body having a proximal end and a distal end and a cannula lumen extending a length of the body;
    a dissection tool adapted to slide within the cannula lumen, the dissection tool including a viewing device, a tissue separating member and an electrode adapted to acutely stimulate the nerve region or nerve branch; and
    a cradle assembly adapted to slide within the cannula lumen, the cradle assembly having a first leg and a second leg extending proximally from a C-ring generally adapted to cradle a portion of the nerve region or nerve branch, an electrode cuff adapted to be disposed over an exterior surface of the C-ring, and a deployment device adapted to deploy the electrode cuff from the C-ring.

2. The surgical apparatus of claim 1, wherein the dissection tool further includes an aperture, wherein the at least one electrode is adapted to be extended and retracted through the aperture.

3. The surgical apparatus of claim 1, wherein the cradle has an exterior surface and an interior surface, the cradle comprising at least one electrode located on the interior surface, wherein the electrode is adapted to acutely stimulate the nerve region or nerve branch.

4. The surgical apparatus of claim 1, wherein the electrode cuff comprises a preformed cuff including at least one electrode disposed on an interior surface of the cuff, the electrode cuff adapted to wrap around the nerve or nerve branch when deployed.

5. The surgical apparatus of claim 4, wherein the preformed cuff includes at least one anode and at least one cathode disposed on the interior surface of the cuff, the at least one anode and at least one cathode adapted to chronically stimulate the nerve.

6. The surgical apparatus of claim 4, wherein the electrode cuff comprises a microstimulator.

7. The surgical apparatus of claim 6, wherein the microstimulator is tethered to the electrode cuff assembly.

8. The surgical apparatus of claim 1, wherein the electrode cuff comprises a preformed cuff adapted to wrap around the nerve region or branch and a microstimulator coupled to the electrode cuff.

9. The surgical apparatus of claim 1, further comprising one or more surgical tools adapted to be extended and retracted through a cannula lumen.

10. The surgical apparatus according to claim 1, wherein the nerve region or nerve branch is located along a vagus nerve.

11. A surgical apparatus for use with a cannula including an endoscopic dissection tool to deploy an electrode cuff about a target nerve site, the surgical apparatus comprising:
    a cradle assembly including a first leg and a second leg extending proximally from a C-ring generally adapted to cradle a portion of a nerve, wherein the C-ring has an exterior surface and an interior surface, the cradle comprising at least one electrode located on the interior surface, wherein the electrode is adapted to acutely stimulate the nerve region or nerve branch;
    an electrode cuff coupled to an exterior of the cradle; and
    a deployment device adapted to deploy the electrode cuff from the cradle to the target nerve site.

12. The surgical apparatus according to claim 11, wherein the dissection tool comprises at least one electrode adapted to acutely stimulate the portion of the nerve.

13. The surgical apparatus of claim 11, wherein the electrode cuff comprises a preformed cuff adapted to wrap around the portion of the nerve when deployed and at least one electrode adapted to chronically stimulate the portion of the nerve disposed on an interior surface of the cuff.

14. The surgical apparatus of claim 13, wherein the electrode cuff comprises a microstimulator.

15. A method for gaining access to and stimulating a targeted nerve region or nerve branch, the method comprising:
    accessing the targeted nerve region or nerve branch using a surgical apparatus comprising a cannula, a dissection tool including a viewing device and an electrode for acutely stimulating the nerve, and a cradle assembly including a C-ring and an electrode cuff including at least one electrode adapted to chronically stimulate a nerve, the electrode cuff disposed over an exterior surface of the C-ring and adapted to be deployed from the exterior surface of the C-ring to a nerve region or nerve branch to be chronically stimulated;
    identifying and isolating potential target nerve regions or nerve branches;
    acutely stimulating potential target nerve regions or nerve branches using the dissection tool electrode or the electrode on the interior surface of the C-ring;
    selecting the target nerve region or branch to receive chronic stimulation;
    deploying the electrode cuff to the target nerve region or nerve branch; and chronically stimulating the target nerve region or nerve branch.

16. The method according to claim 15, where the targeted nerve region is the vagus nerve.

17. The method according to claim 15, wherein the step of selecting the target nerve branch or region to receive chronic stimulation includes using information gained by acutely stimulating potential nerve regions or nerve branches.

18. The method according to claim 15, further comprising using one or more additional surgical tools to further manipulate the potential target nerve region or nerve branch.

* * * * *